United States Patent [19]

Renn

[11] 3,975,162

[45] Aug. 17, 1976

[54] APPLYING REAGENT TO MEDIUM AND DEVICE THEREFOR

[75] Inventor: Donald W. Renn, Glen Cove, Maine

[73] Assignee: Marine Colloids, Inc., Rockland, Maine

[22] Filed: Mar. 13, 1974

[21] Appl. No.: 450,615

[52] U.S. Cl. .............................. 23/253 TP; 424/12
[51] Int. Cl.² ................. G01N 31/06; G01N 33/16
[58] Field of Search .............. 23/253 TP; 195/103.5, 195/127; 424/12

[56] References Cited
UNITED STATES PATENTS

| | | | |
|---|---|---|---|
| 3,092,463 | 6/1963 | Adams, Jr. et al. | 23/253 TP |
| 3,126,325 | 3/1964 | Poole | 195/103.5 R |
| 3,252,762 | 5/1966 | Adams, Jr. et al. | 23/253 TP |
| 3,416,998 | 12/1968 | Streitfeld | 195/103.5 R |
| 3,619,371 | 9/1971 | Crook | 196/103.5 R |
| 3,630,957 | 12/1971 | Rey et al. | 23/253 TP X |

*Primary Examiner*—Robert M. Reese

[57] ABSTRACT

Device for applying a measured quantity of water-soluble or water-dispersible reagent to a water-containing solid medium for use in molecular diffusion or affinity separation procedures is provided in the form of a film consisting essentially of a film-forming solid organic polymeric binder which is soluble in water to the extent of at least 1% by weight at 20°C. and dispersed in said binder a measured quantity of said reagent, said film being of a size and shape adapted to be placed in contact with said medium to permit said reagent and binder to diffuse completely into said medium. The device is used by placing it in face-to-face contact with a water-containing solid medium.

6 Claims, No Drawings

APPLYING REAGENT TO MEDIUM AND DEVICE THEREFOR

This invention relates to an assay device or tool and a method of using the same and pertains more specifically to a device and method for applying a measured quantity of a water-soluble or water-dispersible reagent to a water-containing solid medium for use in molecular diffusion or affinity separation processes.

A variety of analytical procedures have been developed for the separation and identification of different molecular species present in a specimen by applying the specimen to a water-containing solid medium and inducing molecular diffusion of the specimem through the medium. In particular, chromatography and electrophoresis including immunoelectrophoresis processes have been employed, all of which provide separation of different molecular species by differential diffusion of a specimem through a water-containing solid medium. In such processes, a variety of reagents which interact with one or more of the molecular species in the specimem may also be applied to the medium before, during or after the separation process to assist in separation or identification of the species.

These reagents have previously been introduced into the medium in various ways. In some cases, they have been introduced into the medium at the time of manufacture of the latter, but in most cases they have been applied to the surface of the water-containing solid medium at the time they are needed, either by applying a liquid solution or dispersion of the reagent to the surface of the medium and allowing it to stand or by immersing the solid medium in a solution or dispersion of the reagent in a suitable liquid vehicle. In either case, precise measurement and control of the amount and location in the medium into which the reagent diffuses is difficult and uncertain. It has also been proposed to disperse such reagents in a solid water-resistant binder as in Rey et al U.S. Pat. No. 3,630,957 and Sherelis U.S. Pat. No. 3,694,163; and to maintain a reagent-containing solid water-insoluble binder in contact with the surface of a water-containing or absorbing medium such as paper, as in Verbeck U.S. Pat. No. 3,672,845. However, reagents in water-resistant or water-insoluble binders cannot readily be completely extracted and diffused into a water-containing solid medium, making control and measurement of the quantity introduced into the medium impractical.

The present invention provides a device and method which facilitates precise and quantitative introduction of reagent into a solid water-containing medium for use in molecular diffusion or affinity separation procedures. The invention has particular utility in conjunction with a thin layer medium, i.e., a water-containing solid medium in the form of a layer having a thickness of 0.1 to 2 mm. The device of the present invention comprises a film consisting essentially of film-forming solid organic polymeric binder which is soluble in water to the extent of at least 1% by weight at 20°C., and dispersed in the binder a measured quantity of water-soluble or water-dispersible reagent, the film being of a size and shape adapted to be placed in contact with a water-containing solid medium for use in molecular diffusion or affinity separation processes to permit the reagent and the binder to diffuse completely into the medium. By binders which are "soluble in water," it is intended to include those materials which form colloidal solutions or dispersions as well as those which form true solutions.

The binders which can be used in the present invention include various polymeric materials such as dextran, water-soluble polyacrylamide, polyacrylic acid and water-soluble metal salts thereof, water-soluble polyvinyl alcohol, polyethylene glycol, polyethylene oxide, polyvinyl pyrrolidone, clarified guar gum, water-soluble carboxymethyl cellulose, water-soluble hydroxyethyl cellulose, water-soluble methyl cellulose, algin, carrageenan, xanthan gum, starch, water-soluble copolymers of maleic anhydride with various vinyl monomers as described, for example, in U.S. Pat. No. 2,047,398, particularly copolymers of maleic anhydride with vinyl ethers or vinyl esters or their corresponding salts. There can also be present along with the binder conventional humectants or surface-active agents (dispersing agents) to maintain the flexibility of the binder and to facilitate or accelerate its dispersion or dissolution in water.

The film of polymeric binder may be of any desired thickness but is preferably from 0.01 to 2 mm. It may be provided with a temporary removable support or backing in the form of paper or water-insoluble plastic film, but such backing or support is important only for extremely weak or fragile films and may be omitted in the case of self-supporting films. When a support or backing is employed, it is desirably transparent; suitable backings include those formed of such plastics as polyesters, polystyrene, cellulose acetate, polyamides and the like of varying thickness. The thickness of the backing is usually kept to a minimum in order to minimize cost while at the same time providing the desired mechanical reinforcement or strength. The extene of bonding of the reagent-binder film to the backing film is not critical; sufficient bonding is usually provided if the binder film is formed in situ on the surface of the backing film from a solution or a melt.

The reagents which can be incorporated in the film of polymeric binder can be any of the water-soluble or water-dispersible materials, many of which are commonly employed in assay procedures, such as antibodies, antigens, enzymes, enzyme substrates, precipitin brighteners, stains, precipitants, microbiological organisms and/or nutrients therefor, buffers, salts and the like as well as radioactively tagged or fluorescent reagents of the foregoing types.

The relative proportions of reagent and of water-soluble polymeric binder in the device can be varied widely depending upon the size or amount of the measured quantity which is desired and is a matter of choice or convenience. Usually it is most convenient to employ a device in which the water-soluble polymeric binder amounts to about 10 to 95% by weight of the film while the reagent constitutes the remainder. Two or more different reagents can be employed in admixture with each other; a mixture of two or more different polymeric binders can also be employed although usually there is no advantage in using such a mixture.

The reagents can be incorporated in the film of polymeric binder in a variety of ways bearing in mind that it is usually important to have the reagent distributed as uniformly as possible throughout the mass of polymeric binder. The reagent can be mixed with the polymeric binder while the latter is in molten form or in the form of a solution in a volatile solvent, after which the mixture is formed into a film of the desired thickness and allowed to dry or to cool in order to solidify it. The film of water-soluble polymeric binder can also be formed separately from a solution of the binder or from a melt, after which a solution or dispersion of the reagent in a suitable liquid vehicle can be applied to the surface of the film, allowed to diffuse into the film, and the film dried. In some cases, the reagent in dry, finely-divided particulate form can be spread on the surface of the film of water-soluble polymeric binder after which the latter is melted and resolidified. While forced air drying can usually be employed in forming the film and/or incorporating the reagent in the film, vacuum or freeze-dryng can also be employed in the case of heat-sensitive materials.

The size of the device of the present invention is a matter of choice depending upon the nature of the assay procedure being carried out. Generally, it is not convenient to employ devices in which the dimensions of the film are less than about 5 mm. square, but smaller devices can be employed in special cases where it is desired to confine the reagent to a small localized area of the medium, and larger devices can be employed including those large enough to cover the entire exposed surface of the medium to which the reagent is to be applied, which may be of the order of 15 sq. inches or even more. The film may be of any desired shape, including annular or perforated.

The devices of the present invention can be employed in applying reagents to any water-containing solid medium used in molecular diffusion of affinity separation procedures, such as, for example, chromatography and electrophoresis, particularly those in the form of thin layers (i.e., having a maximum thickness of 2 mm.) whether in the form of a gel, membrane, cellular product or tissue. Of particular importance are hydrated gels formed of agarose, agar, polyacrylamide (cross-linked to prevent dissolution), or cellulose acetate; paper and cellulose acetate membranes are also of importance.

In using the device of the present invention, the face of the reagent-containing film is simply placed in contact with the water-containing solid medium and allowed to remain there until complete dissolution or diffusion of the reagent and polymeric binder occurs and the reagent and binder diffuse into the medium. This step is usually carried out at room temperature although other temperatures from 1° to 60°C. can also be employed. When a water-insoluble backing or support is provided for the film as a part of the device, it may be allowed to remain in place on the surface of the water-containing medium, or if desired, it can be removed when diffusion of the reagent and binder is complete. The device can also be used to introduce reagents into media used for culturing bacteria, and can be used for histological staining by applying a stain-containing device in contact with tissue.

The following specific examples are intended to illustrate the nature of the invention without acting as a limitation upon its scope.

EXAMPLE 1

A solution of Lactic Dehydrogenase (LDH) localizing reagent was prepared from a commercially available substratedye and buffer mixture. To 1 ml. of this solution was added 9 ml. of a 0.5% be weight water solution of polyethylene glycol 4000 binder and the mixture stirred. Five ml. of this mixed solution was then placed evenly on a 3¼ × 4 inch backing or support film of water-insoluble hydrophilic polyethylene terephthlate sold under the trade name "Cronar" and rapidly dried at 40°C. in a forced air oven to form a binder—LDH film approximately 0.02 mm. thick on the backing.

A conventional hydrated agarose electrophoresis medium (a layer of hydrated agarose 1-2 mm. thick on a support of Cronar film) was equilibrated with standard aqueous buffer solution, inoculated with human serum, and subjected to electrophoresis. After completion of the electrophoresis, the LDH-binder film was placed on the agarose medium with the backing uppermost and the sandwich assembly was placed in an incubator at 37°C. for one hour. Visible purple lines appeared in the medium identifying the location of the serum components with which the LDH had reacted. The backing film was then removed from the surface of the medium, the latter was washed briefly in running water, then soaked in 5% by weight aqueous acetic acid to fix the colored lines and dried to form a permanent record.

If desired, the reagent-binder film after preparation can be stored indefinitely before use by enclosing in a bag of 3 mil polyethylene and maintaining at 4°–8°C.

EXAMPLE 2

The same type of reagent-binder film as in Example 1 was prepared except that the solution of polyethylene glycol 4,000 was placed separately on the backing film and dried. The LDH visualization solution (1 ml.) was then evenly distributed on the surface of the polyethylene glycol 4,000 and dried. The device so produced was used in the same procedure as described in Example 1.

EXAMPLE 3

To 10 ml. of a 0.5% water solution of polyvinyl pyrrolidone binder was added 0.4 ml. of anti-whole human serum prepared in goats as the reagent and the mixture stirred briefly. Five milliliters of this was distributed on a 3¼ × 4 inch backing film as in Example 1 and dried at 25°C. in a forced air oven to form a reagent-binder film approximately 0.1 mm. thick on the backing film.

The device so prepared was used by placing the reagent-binder film in contact with the surface of a 3¼ × 4 inch plain hydrated agarose electrophoresis film medium provided with the usual sample wells for electroimmunodiffusion. After 30 minutes at room temperature, the backing film was removed, the sample wells were cleared of residual liquid, and specimens of serum were introduced into the wells. After electrophoresis for 45 minutes at 100 V. the desired visible "rocket" precipitin patterns had developed where interaction of the reagent with the serum constituents had occurred.

EXAMPLE 4

The reagent-binder film prepared as described in Example 3 was placed in contact with a freshly prepared 1% aqueous agarose gel medium 1 mm. thick containing 0.85% sodium chloride and 0.05% sodium azide in which two 2 mm. diameter wells were cut for radialimmunodiffusion. After 30 minutes at room temperature, the backing film was removed and the residual fluid removed from the wells. Five microliter specimens of human serum were placed in the wells and the gel medium placed in a humidity chamber. After 24 hours, the gel showed the desired precipitin rings around the wells showing the location of reaction products of the serum and the reagent after diffusion.

EXAMPLE 5

A reagent-binder film useful for the procedures described in Examples 3 and 4 can also be prepared by mixing 0.4 ml. of the antisera with 10 ml. of a 0.5% aqueous polyvinyl pyrrolidone binder solution, freeze drying the mixed solution, and spreading the freeze-dried solid on a plastic backing either on a thin layer of wet polyvinyl pyrrolidone film or other contact adhesive.

EXAMPLE 6

The same procedure was followed as in Examples 3, 4 and 5 except that the antigen, normal human serum, was used as the reagent in the binder film and the antibody was used as the test specimen.

EXAMPLE 7

The same procedure was used as in Example 3 except that in place of polyvinyl pyrrolidone binder there were used, respectively, polyvinyl alcohol, polyethyleneoxide, polyethyleneglycol 20,000, polyacrylamide (water-soluble), sodium alginate, methylcellulose, clarified guar gum, water-soluble hydroxyethyl cellulose, xanthan gum, soluble starch, and dextran as the binder. In addition, there were substituted for the backing film films of polyvinylidene chloride (Saran Wrap), polycarbonate, polymethyl methacrylate, and cellulose acetate, all of which are water-insoluble. Self-supporting films of reagent-binder were prepared from the foregoing mixtures by employing polytetrafluoroethylene film (Teflon) as the backing, then stripping the dried reagent-binder film from the backing before use.

EXAMPLE 8

A 0.2 g. quantity of lipoprotein stain Fat Red 7B (Sigma) was dissolved in 0.2 ml. polyethylene glycol 400 and the mixture thoroughly stirred into 2 grams of molten polyethylene glycol 4000, then the mixture was spread quickly and evenly on a 3¼ × 4 inch backing film of hydrophilic polyethylene terephthalate and allowed to harden. The film was used without further change by placing the reagent-binder surface in contact with the surface of a hydrated agarose gel medium in which serum protein had previously been subjected to electroporesis. After 10 minutes contact at room temperature, the backing film was removed, whereupon the bands or reacted lipoprotein were visible in the medium.

In another embodiment, there was added to the reagent-binder mixture 0.01 g. of a nonionic surface-active agent, octyl phenoxy polyethoxy (9–10) ethanol sold under the trade name Triton X-100. The reagent-binder film so prepared exhibited more rapid diffusion into the agarose gel medium.

EXAMPLE 9

Equal volumes of 0.08 ionic strength pH 8.2 barbital buffer and 1% aqueous polyethylene glycol 4000 binder were mixed; 5 ml. of this mixture was poured onto the surface of a 4 mil hydrophilic polyethylene terephthalate backing film and dried in a forced air oven at 40°C. The resulting reagent-binder film approximately 0.5 mm. thick was placed in contact with the surface of a hydrated agarose gel film medium approximately 2 mm. thick, leaving the backing film in place on the side of the reagent-binder film away from the medium. After 10 minutes at room temperature, the backing film was removed and the gel medium was ready to receive a test specimen prior to an electrophotetic procedure.

EXAMPLE 10

Dextran sulfate, a specific precipitant for lipoproteins, can be used as such when incorporated in a reagent-binder film. About 0.5 g. of dextran sulfate reagent was dissolved in 1 ml. of water and spread evenly on the surface of a previously prepared dried film of polyethylene glycol 4,000 binder approximately 0.25 mm. thick, then dried in a forced air oven at 40°C.

Human serum specimens were subjected to electrophoresis in a conventional hydrated agarose gel medium approximately 1 mm. thick supported on a backing of hydrophilic polyethylene terephthalate film. After completion of the electrophoresis, the reagent-binder film surface was placed in contact with the gel medium and allowed to remain for 15 minutes at room temperature, after which the surface of the medium was washed with water. White bands of the precipitated reaction products of lipoproteins with the dextran sulfate were visible in the medium, measurement of which made possible the determination of the quantity of lipoproteins.

EXAMPLE 11

A reagent-binder film was prepared by distributing 1 ml. of a 1:5 alpha$_1$ antitrypsin antisera reagent in 0.85% saline solution evenly on the surface of a previously prepared and dried film of polyethylene glycol 6,000 binder approximately 0.25 mm. thick. The resulting product was rapidly dried at 20°C. This reagent-binder film was used in the manner described in Example 10 for pi typing human serum after electrophoretic runs.

What is claimed is:

1. The process of analyzing a specimen by subjecting it to a molecular diffusion separation procedure in a water-containing solid medium and causing constituents of the specimen to react with a reagent in said medium, wherein the improvement comprises
providing a measured quantity of water-soluble or water-dispersible reagent incorporated within a solid film of solid film-forming organic polymer binder which is soluble in water to the extent of at least 1% by weight at 20°C.,
placing one face of said film in contact with said water-containing solid medium and maintaining it in contact for sufficient time to permit said reagent and binder to diffuse completely into said medium.

2. The process as claimed in claim 1 in which said device includes a supporting backing of water-insoluble synthetic plastic bonded to the other face of said film.

3. The process as claimed in claim 2 including the additional step of removing said supporting backing after said diffusion is complete.

4. Device for applying a measured quantity of water-soluble or water-dispersible reagent to a water-containing solid medium for use in molecular diffusion or affinity separation procedures, said device comprising
a solid film consisting essentially of a film-forming solid organic polymeric binder which is soluble in water to the extent of at least 1% be weight at 20°C. and incorporated within said binder film a measured quantity of said reagent, said film being of a size and shape adapted to be placed in contact with said medium to permit said reagent and binder to diffuse completely into said medium.

5. A device as claimed in claim 4 including a supporting backing of water-insoluble synthetic plastic bonded to one face of said film.

6. A device as claimed in claim 5 in which said binder is selected from the group consisting of dextran, polyacrylamide, polyacrylic acid, polyvinyl alcohol, polyethylene gylcol, polyethylene oxide, polyvinyl pyrrolidone, guar, carboxymethyl cellulose, hydroxyethyl cellulose, methyl cellulose, algin, carrageenan, xanthan gum, starch, and copolymers of maleic anhydride with vinyl monomers.

* * * * *

UNITED STATES PATENT AND TRADEMARK OFFICE
CERTIFICATE OF CORRECTION

PATENT NO. : 3,975,162
DATED : August 17, 1976
INVENTOR(S) : Donald W. Renn

It is certified that error appears in the above-identified patent and that said Letters Patent are hereby corrected as shown below:

Column 2, line 34, "extent" is misspelled;

Column 3, line 12, "freeze-drying" is misspelled;

Column 3, line 29, "of" should be --or--;

Column 3, line 46, "1°to" should be --1°C. to--;

Column 3, line 63, "substratedye" should be --substrate-dye--;

Column 3, line 64, "be" should be --by--;

Column 5, line 46, "electrophoresis" is misspelled;

Column 5, line 48, "or" should be --of--;

Column 6, line 3, "electrophoretic" is misspelled;

Column 6, line 63, "be" should be --by--.

Signed and Sealed this

Nineteenth Day of October 1976

[SEAL]

Attest:

RUTH C. MASON
*Attesting Officer*

C. MARSHALL DANN
*Commissioner of Patents and Trademarks*